(12) United States Patent
Hansen et al.

(10) Patent No.: US 7,047,077 B2
(45) Date of Patent: May 16, 2006

(54) CONNECTOR PORT CONSTRUCTION TECHNIQUE FOR IMPLANTABLE MEDICAL DEVICE

(75) Inventors: David J. Hansen, Oakdale, MN (US); Scott A. Tolson, Arden Hills, MN (US); Scott A. Spadgenske, Fridley, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 515 days.

(21) Appl. No.: 10/222,151

(22) Filed: Aug. 16, 2002

(65) Prior Publication Data

US 2004/0034393 A1 Feb. 19, 2004

(51) Int. Cl.
*A61N 1/375* (2006.01)
(52) U.S. Cl. ............................................. 607/37
(58) Field of Classification Search ................. 607/37, 607/38; 439/909
See application file for complete search history.

(56) References Cited

U.S. PATENT DOCUMENTS

| | | | | |
|---|---|---|---|---|
| 4,245,642 A | * | 1/1981 | Skubitz et al. | 607/37 |
| 4,898,173 A | * | 2/1990 | Daglow et al. | 607/37 |
| 4,934,366 A | * | 6/1990 | Truex et al. | 607/37 |
| 4,934,367 A | * | 6/1990 | Daglow et al. | 439/527 |
| 4,942,876 A | * | 7/1990 | Gotthardt | 607/37 |
| 5,070,605 A | * | 12/1991 | Daglow et al. | 29/842 |
| 5,324,311 A | * | 6/1994 | Acken | 607/37 |
| 6,029,089 A | | 2/2000 | Hawkins et al. | |
| 6,044,302 A | | 3/2000 | Persuitti et al. | |
| 6,052,623 A | | 4/2000 | Fenner et al. | |
| 6,192,276 B1 | * | 2/2001 | Strandberg | 607/36 |
| 6,208,900 B1 | * | 3/2001 | Ecker et al. | 607/17 |
| 6,321,126 B1 | * | 11/2001 | Kuzma | 607/137 |

* cited by examiner

*Primary Examiner*—George Manuel
*Assistant Examiner*—Lenwood Faulcon, Jr.
(74) *Attorney, Agent, or Firm*—Nikolai & Mersereau, P.A.; Thomas J. Nikolai

(57) ABSTRACT

A connector port or "header" for an implantable medical device comprises a molded plastic connector module having a longitudinal bore formed therethrough and a plurality of slots formed inwardly of one side surface thereof and intersecting the longitudinal bore. The slots receive electrical contact members therein and individual seal members are inserted through the longitudinal bore between each of the contact members such that when the in-line terminal pin of a medical lead is inserted into the longitudinal bore, contacts on the lead terminal are aligned with and mate to the electrical contacts in the connector block. The seal members prevent body fluids from compromising the resulting electrical connection.

14 Claims, 5 Drawing Sheets

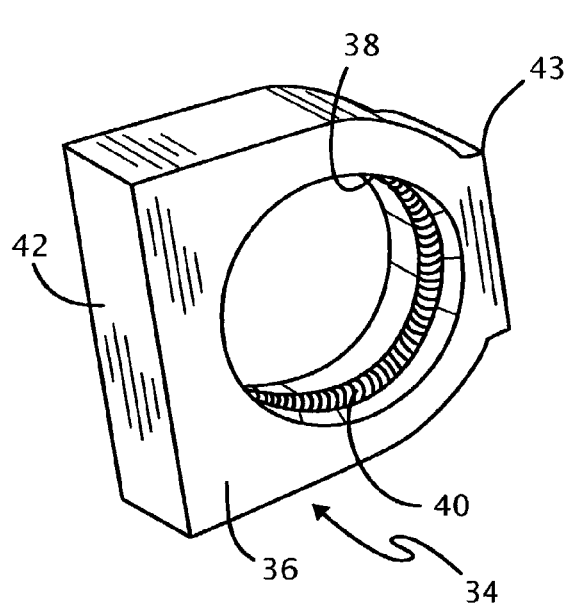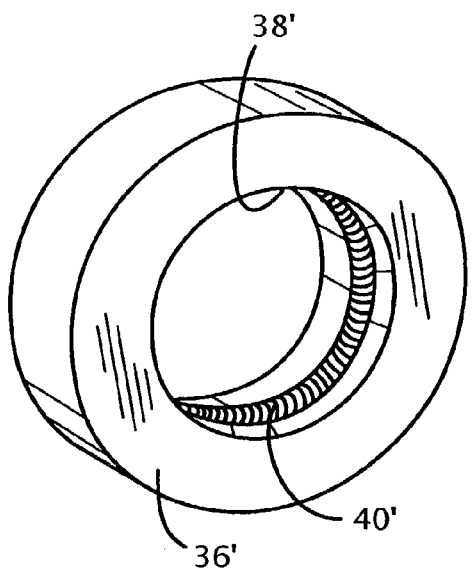
FIG. 3A    FIG. 3B
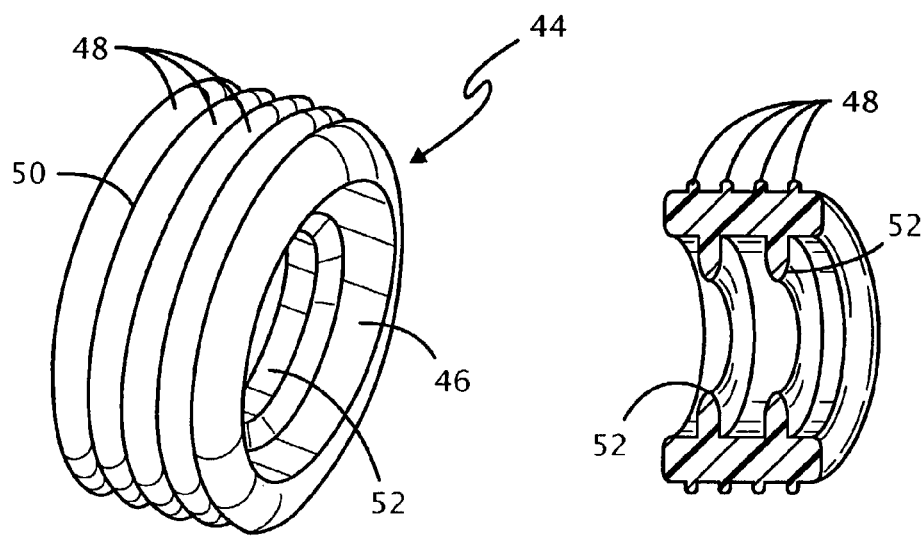
FIG. 4A    FIG. 4B

CONNECTOR PORT CONSTRUCTION TECHNIQUE FOR IMPLANTABLE MEDICAL DEVICE

BACKGROUND OF THE INVENTION

I. Field of the Invention

This invention relates generally to implantable medical devices in which an electronic circuit and a power source are contained within a hermetically sealed enclosure and having a feedthrough with multiple input and output pins, and more particularly to a connector port for such a device for facilitating the attachment of electrodes on a lead to the input and output pins for the circuitry within the hermetically sealed enclosure.

II. Discussion of the Prior Art

Over the past 30 years great strides have been made in increasing the functional performance of and decreasing the physical size of implantable medical devices, such as those designed for cardiac rhythm management and neural stimulation. Generally speaking, current state-of-the-art implantable medical tissue stimulating devices incorporate a battery power supply and a microprocessor-based controller that is designed to control a pulse generator, causing it to issue pulses at times determined by the microprocessor-based controller. The pulses are conveyed to target tissue on or in the heart by means of one or more medical leads having sensing/stimulating electrodes at a distal end and the electrodes connected by lead conductors to electrical contacts on a connector pin located at the proximal end of the lead. The lead connector connects the lead to the pulse generator.

While a variety of lead connectors have been devised, a major improvement in lead connectors has been the low profile, in-line bipolar design. An in-line connector places both electrical terminals on a single lead pin, with an insulating barrier separating the anode contact from the cathode contact. To facilitate compatibility between pulse generators and leads of differing manufacturers, standards have been developed. More particularly, a joint IEC and International Standards Organization (the International Pace Standards Working Group) has defined the parameters of a low-profile connector referred to as IS-1 for unipolar and bipolar leads and DF-1 for defibrillator leads.

Additionally, there is ongoing work to develop AAMI and Potentially ISO standards for connectors for tripolar and quadrapolar leads.

As those skilled in the art appreciate, the lead connector must be mechanically and electrically secured to the implantable device in a way that remains secure following implantation, but which can be readily detached if and when it becomes necessary to install a new pulse generator. The Persuitti et al. U.S. Pat. No. 6,044,302 describes a connector port for an implantable pulse generator that can accommodate a plurality of in-line lead terminal pin having multiple contacts. In the '302 patent, a lead port has one or more connector blocks each including a set screw to lock the lead connector in contact with the connector block. The connector blocks are, in turn, connected to a feed-through wire. A single elastomeric seal is provided within the port such that when the connector pin is inserted therethrough, it precludes ingress of body fluids into the bore in the header. It is also known in the art to provide sealing rings on the lead terminal connector itself for creating a fluid impervious seal upon insertion of the lead into a connector port. In this regard, reference is made to the Hawkins et al. U.S. Pat. No. 6,029,089.

Prior construction techniques have relied on radial insertion of seal members into a connector bore as well as the use of adhesives to provide bonding and/or sealing. This prior art method exhibits three primary disadvantages. The first is that radial or side loading of the inner seals into the connector block assembly is often a problematic assembly step that can result in non-uniform loading and subsequent deformation of the seal. This creates not only a inferior manufacturing process, but the resultant deformation often translates into highly variable insertion forces between the lead connector and the connector port. Secondly, multi-port device connectors using radially loaded seals often integrate seals between lead bores to help reduce the manufacturing impact. This creates the potential for cross-chamber leakage, since the lead barrels are no longer isolated by the material comprising the connector block. Finally, conventional radial or side-loaded seals often rely on the application of additional medical adhesive to bond and retain the seals inside the header. This results in an undesirable manufacturing process in that the adhesive requires additional steps and frequently ends up in unintended areas.

A need, therefore, still exists for a connector port for an implantable medical device capable of accommodating multiple feedthrough pins and lead connector contacts that remain small in size, easy to assemble, and which exhibits a low insertion force. The present invention provides an efficient and effective means for manufacturing sealed, axially aligned, multi-electrode connector ports for use with implantable medical devices that minimizes the need for medical adhesives. The connector port of the present invention provides mechanical retention, sealing and electrical contact with mating, slidable, smooth, implantable lead connectors.

SUMMARY OF THE INVENTION

The present invention is directed to a connector port for an implantable medical device of the type comprising an electronic circuit and a power source contained within a hermetically sealed housing that has a feed-through assembly with a plurality of input and output pins. The connector port comprises a molded plastic header having one or more longitudinal bores adapted to receive a lead connector pin therein. The header further includes a plurality of parallel spaced-apart, transversely extending, slots that are formed through one side edge of the connector block and which intersect the longitudinal bore(s). A plurality of electrical contact members that are sized to conform to the shape and dimensions of the slots are inserted into the slots. The contact members each comprise a metal plate of uniform size and shape having a central aperture formed therethrough and disposed in the aperture is a terminal engaging member. Without limitation, the terminal engaging member may preferably comprise a toroidal, canted-coil metal spring or an end of a set screw. Following insertion of a first contact member, a tubular elastomeric seal member is inserted in a longitudinal direction through the bore in the connector block. The seal member is pushed up against a side surface of a metal plate of the previously inserted electrical contact member and following insertion of that seal, a next adjacent electrical contact member is inserted into its transversely extending slot, followed by placement of another tubular seal member. These steps are repeated until all of the electrical contact members and tubular seal members have been inserted into the header. The populated header is then attached to the medical device housing and the feed-through wires are welded to the electrical contact members.

DESCRIPTION OF THE DRAWINGS

The foregoing features, objects and advantages of the invention will become apparent to those skilled in the art from the following detailed description of a preferred embodiment, especially when considered in conjunction with the following drawings in which like numerals in the several views refer to corresponding parts.

FIG. 3A is a perspective view of one embodiment of the electrical contact members used in the header of FIG. 1;

FIG. 3B is a perspective view of an alternative embodiment of the electrical contact member used in the header of FIG. 1;

FIG. 4A is a perspective view of one of the seal members used in the header of FIG. 1;

FIG. 4B is a cross-sectioned view of the seal member of FIG. 4A;

DESCRIPTION OF THE PREFERRED EMBODIMENT

Figure 1:
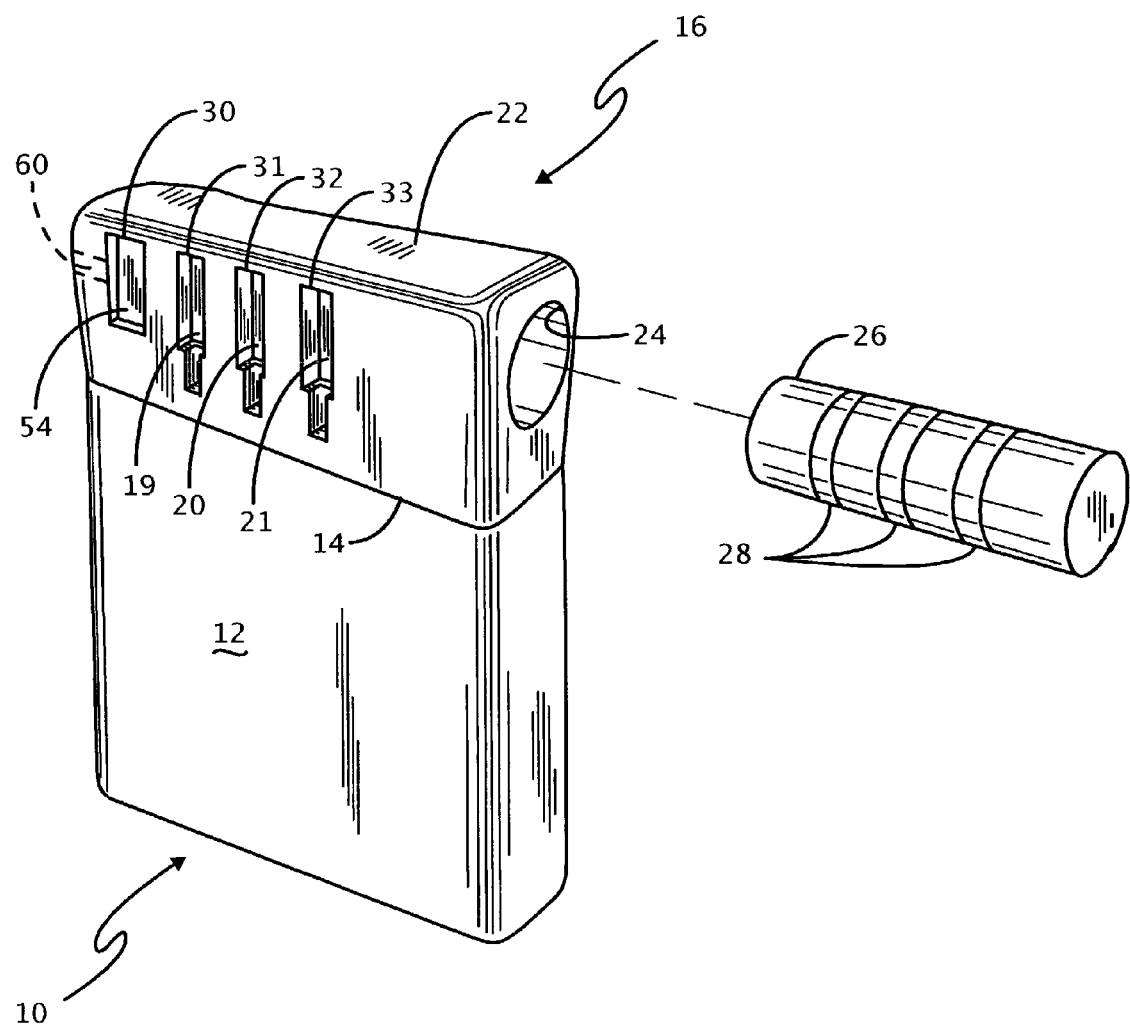
FIG. 1 is a perspective view of an implantable medical device incorporating the header comprising a preferred embodiment of the present invention.

Certain terminology will be used in the following description for convenience in reference only and will not be limiting. The words "upwardly", "downwardly", "rightwardly" and "leftwardly" will refer to directions in the drawings to which reference is made. The words "inwardly" and "outwardly" will refer to directions toward and away from, respectively, the geometric center of the device and associated parts thereof. Said terminology will include the words above specifically mentioned, derivatives thereof and words of similar import.

Referring first to FIG. 1, there is indicated generally by numeral 10 an implantable medical device, such as a pacemaker or defibrillator. The device includes a hermetically sealed housing or can 12 having a top surface 14 to which a header assembly 16 is attached. Fitted into the top surface 14 of the can 12 is a feedthrough assembly that comprises a plurality of conductive pins, as at 19, 20 and 21, that pass through hermetic seals in a feedthrough plate to establish electrical connections between circuitry contained within the housing 12 and contact members contained within the header assembly 16.

The header assembly 16 comprises a plastic module 22 that is molded from a suitable medical grade plastic, such as tecothane. Formed longitudinally through the module 22 is a longitudinal bore 24 into which a lead connector pin 26 is adapted to be inserted. The lead connector pin 26 may be a proprietary design of a given manufacturer or may be constructed in accordance with international standards in terms of its dimensions and spacing between terminal contacts 28.

Figure 2:
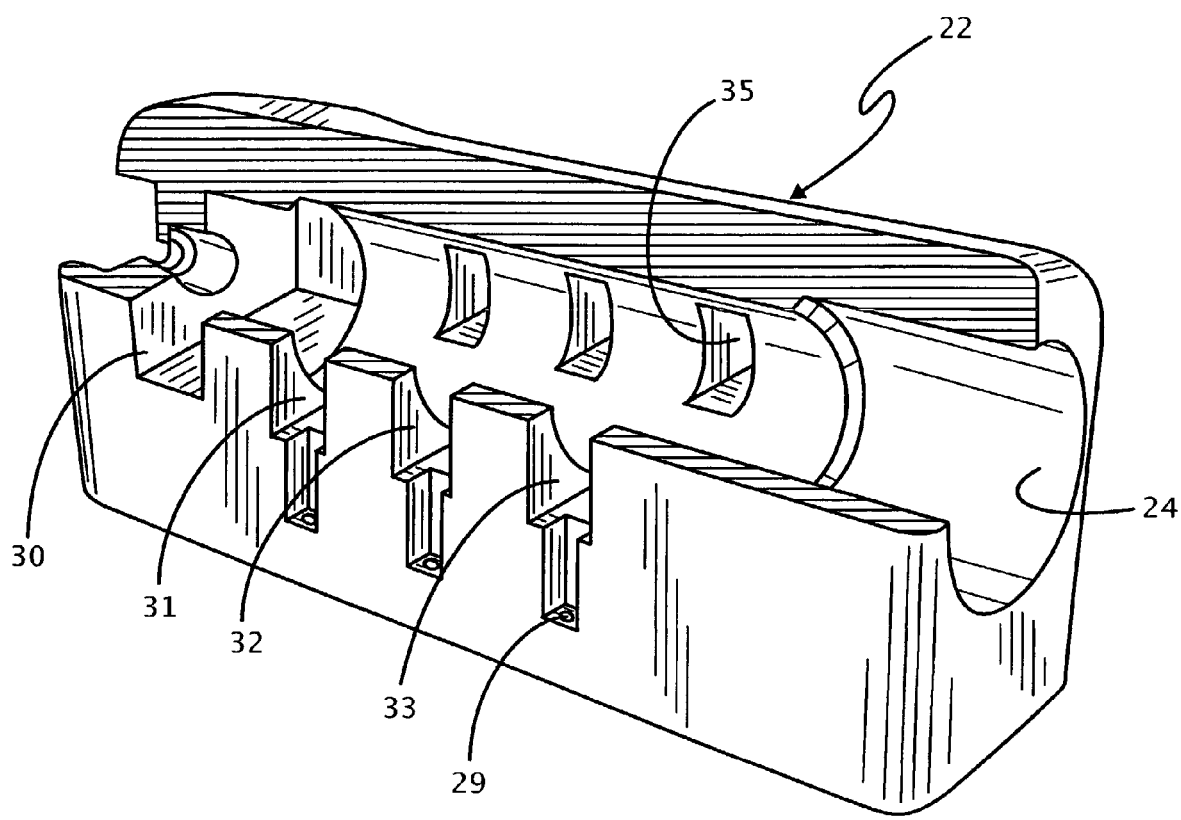
FIG. 2 is a partially sectioned view of the connector module used in the header of FIG. 1.

Referring to the partially sectioned view of FIG. 2, it can be seen that the connector module 22 includes a plurality of transversely extending slots 30, 31, 32 and 33, each of which intersects with the longitudinal bore 24. Formed through the floor of these slots are tiny pinhole apertures 29 through which the feedthrough pins 18–21 may individually pass.

The slots 31, 32 and 33 may be generally D-shaped so as to accommodate insertion of a correspondingly D-shaped electrical contact member therein. One such contact member is indicated generally by numeral 34 in FIG. 3A and comprises a metal plate 36 having a circular bore 38 formed through the thickness dimension thereof. The contact member may also be generally circular in shape as shown in FIG. 3B, in which event the slots are correspondingly shaped. The wall defining the bore 38 (FIG. 3A) or 38' (FIG. 3B) includes an annular recess and, in accordance with one embodiment, there is contained within the recess is a canted-coil spring 40, formed as a ring. The canted coil springs used may be of a type manufactured by Bal Seal Engineering Company and are preferably formed from titanium MP35N, each of which exhibits excellent bio-compatibility. The inside diameter of the spring 40 is slightly less than the diameter of the lead connector pin 26 so as to require a predetermined insertion force to spread the spring and to provide good electrical contact with the lead contacts 28 on the connector pin 26. Those skilled in the art will recognize that electrical contact members different from those specifically described may be used as well. A set screw passing through a threaded bore and intersecting the bore 38 may be used to enhance contact with a lead terminal pin 26. The vertical surface 42 of the D-shaped electrical connector of FIG. 3A or an arcuate surface of the toroidal connection of FIG. 3B is exposed through the slots 31–33 allowing the feedthrough pins 19–21 to be welded to that surface. The D-shaped contacts 34 shown in FIG. 3A include a generally rectangular protuberance 43 projecting radially therefrom which is designed to fit into a recess 35 formed into the connector module 22 across from its entrance slot. Where a toroidal electrical contact member, such as shown in FIG. 3B is used, the module 22 may be formed with rounded slots to accommodate the contact curvature.

Contained within the longitudinal bore 24 between each of the plurality of electrical contact members is a tubular elastomeric seal member, one of which is illustrated in the perspective view of FIG. 4A and is identified generally by numeral 44. Being tubular, it has a longitudinally extending lumen 46 along with integrally formed annular ribs 48 projecting radially outwardly from the surface 50 of the tubular seal member. Similar, but larger, annular protuberances project into the lumen 46 and are identified by numeral 52 (FIG. 4B). The annular projections 48 on the exterior of the seal member cooperate with the diameter of the bore 24 to create a fluid impervious seal while the annular protuberances 52 cooperate with the outside diameter of the lead connector pin 26 to inhibit passage of body fluids. These tubular elastomeric seals are also symmetrical, thus allowing insertion in either direction to facilitate manufacturability.

Important to the manufacturability and attendant cost reduction in fabricating the lead connector port 16 is the fact that the electrical contact elements 34/34' and the seal elements 44 are all identical in size, form and material, thereby reducing the parts count. Moreover, the seal members 44 are designed to be inserted longitudinally down the lead receiving bore 24 rather than being inserted from the side, as in some earlier designs. This helps prevent unwanted deformation of the seal member, thereby providing a more controlled insertion force needed to insert the lead connector 26 down the bore 24.

Figure 5:
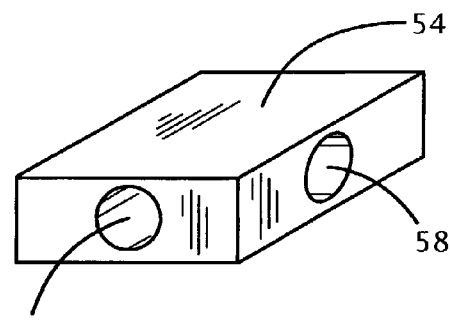
FIG. 5 is a perspective view of a locking block used in the header.

In assembling the header assembly 16, an optional locking block 54, shown in FIG. 5, may first be inserted through the slot 30 formed in the plastic connector module 22. The locking block 54 illustrated herein has a bore 56 formed therethrough of a diameter that is slightly greater than the diameter of the lead connector pin 26. Also formed in the block 54 transverse to the bore 56 is a threaded bore 58. The threaded bore 58 is adapted to receive a set screw therein which can be tightened against the lead connector pin 26 to firmly lock the connector pin 26 within the connector port. If a set screw-type lock is to be avoided, the locking block may instead incorporate a spring-type latch of known construction to positively grip a proximal terminal of a medical lead.

Figure 6:
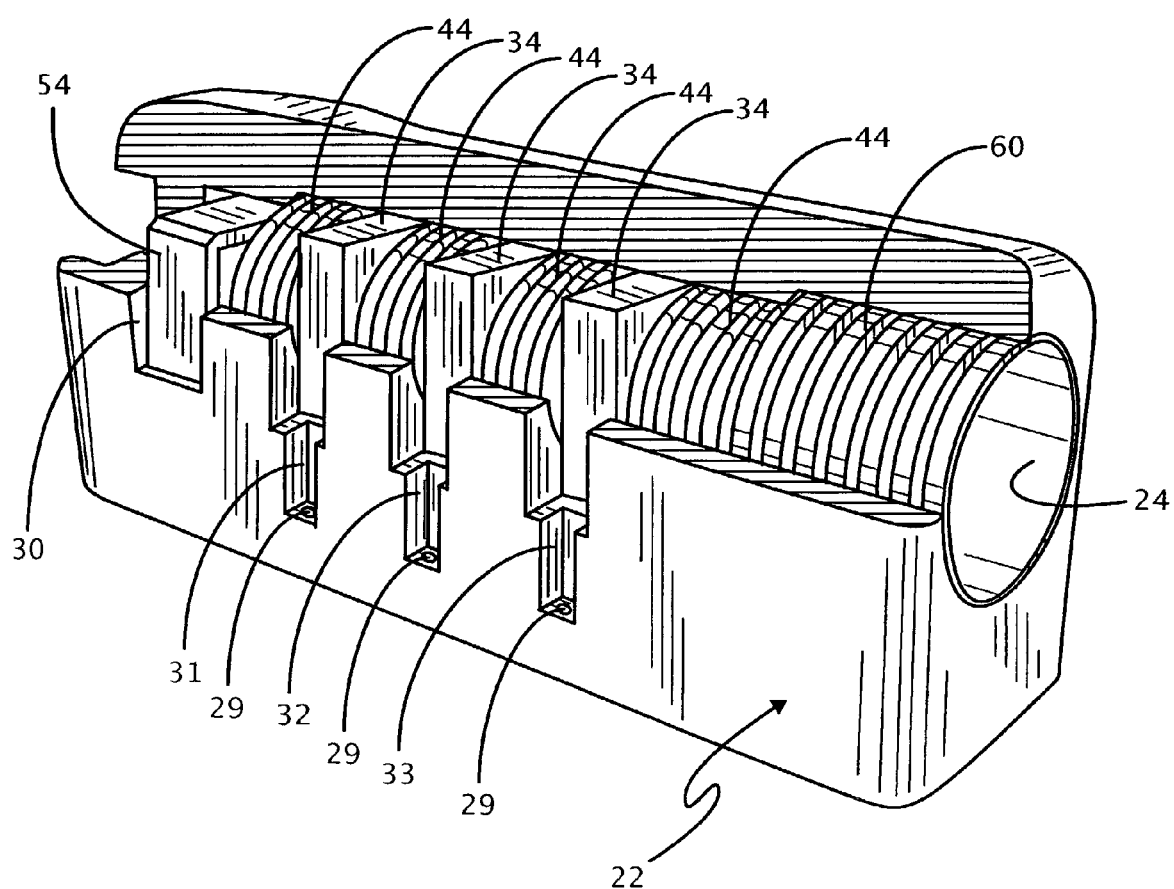
FIG. 6 is a partially sectioned view of a header with the contact members and seal members inserted in the connector module.

Once the locking block 54 is inserted through the slot 30, a seal member 44 is pushed with an appropriate tool down the longitudinal bore 24 until the seal's distal end abuts a facing surface of the locking block 54. Next, an electrical contact member 34 is inserted through the slot 31 so that its protuberance 43 seats in recess 35. Following that, another seal member 44 is pushed down the longitudinal bore 24 until it abuts the electrical contact member that had been inserted through the slot 31. This process is repeated until both slots 32 and 33 are populated with electrical connector members 34 and with a seal member 44 between them. Another elastomeric seal member 44 is then inserted through the longitudinal bore 24 until its distal end abuts the metal plate of the electrical connector in the slot 33. Finally, a tubular end seal 60 is inserted and bonded, completing the assembly steps. A fully assembled lead connector block is shown in the sectioned perspective view of FIG. 6.

Because the spacing between the slots 30–33 are established by the mold used to fabricate the plastic part 16, and because of the manner in which the electrical contact members and seal members are inserted, there is no cumulative tolerance buildup problem that would occur if the contacts and seals are both inserted through the longitudinal bore 24 as in possible alternate designs. In the case of the present invention, the electrical contact plates act as stops for the seals, properly registering each. Also, the apertures 38 and the lumens 46 all become concentrically aligned within the bore 24, thus providing a predictable insertion force. Without limitation, the seal members 44 and 60 are preferably made of 3D silicone and are relatively soft so as to allow conformance to and sealing with the wall of the bore 22 and the surface of a connector pin 26.

Figure 7:
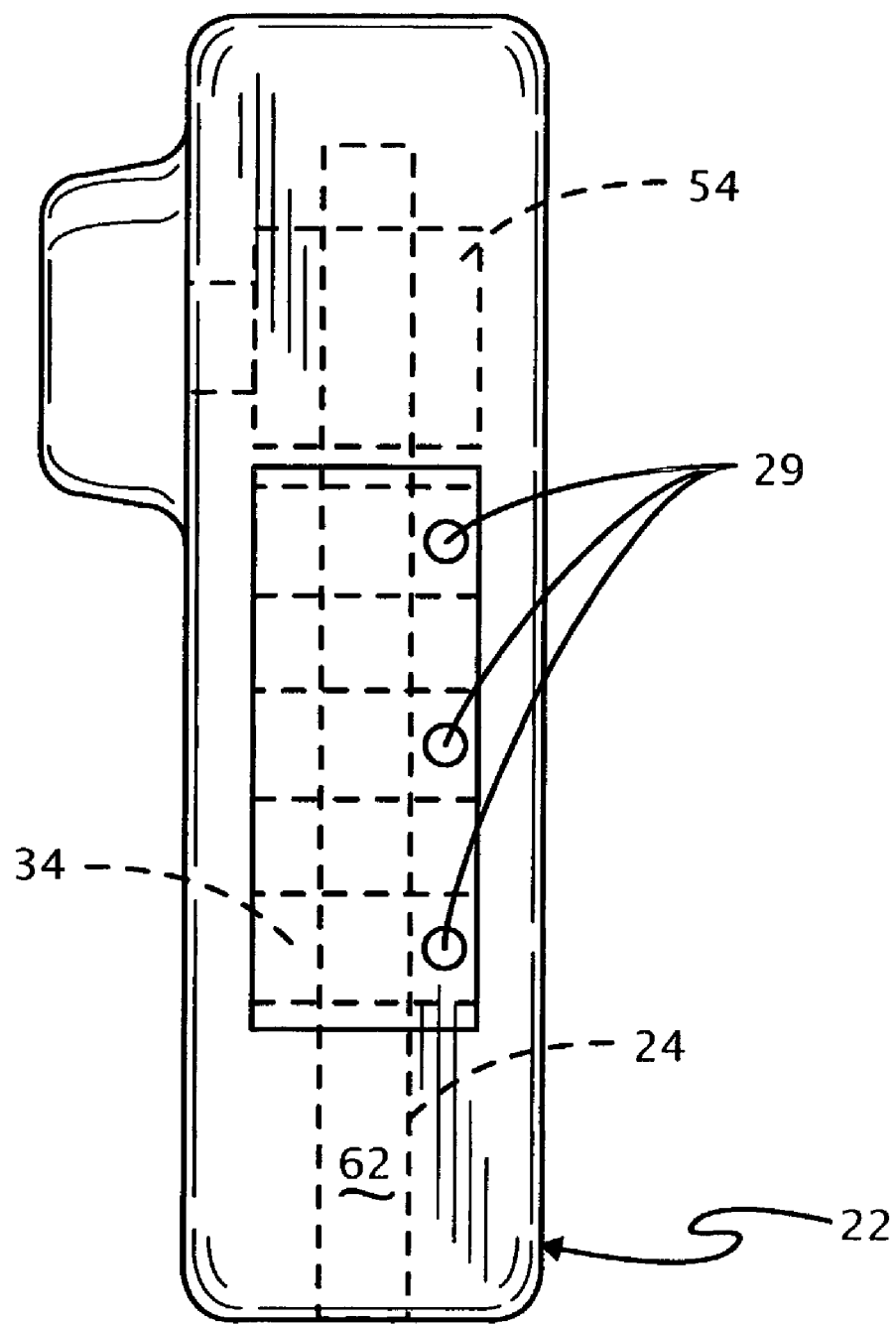
FIG. 7 is a bottom view of the assembled header prior to its attachment to a pulse generator housing.

FIG. 7 is a bottom view of the lead connector block 22 and formed inwardly of a bottom surface 62 thereof is a generally rectangular recess 64 that is adapted to receive a flange plate of a feed-through assembly welded to the header 14 of the can or housing 12. This allows the surface 62 to contact the can whereby a suitable bonding agent may be used to affix the lead connector module or header 22 to the can of the implantable medical device. Also visible in the bottom view of FIG. 7 are pin-hole apertures 29 through which feedthrough pins pass before they are laser welded to the exposed side surfaces of the electrical connector members 34.

It has been found expedient when using a locking block with a spring latch member to also provide a gas relief vent that extends through the plastic connector module 22 downstream of the locking block 30 so that there will be no buildup of air pressure as the lead connector pin 26 is being seated within the bore 24 of the header 16. In FIG. 1, a pressure relief bore 60 serves as the vent. The vent hole 60 is sized appropriately to allow for fluid escape, but still small enough to maintain a specified impedance required for proper functioning of the medical device. A ISO Standard specifies that the required resistance of saline at 37° C. and 9 grams per liter concentration within a hole be 50,000 ohms. This insures that signals from the heart are not shunted, causing sensed signals to be compromised. In general, 50,000 ohms is in excess of 10 times the maximum source impedance of intracardiac signals seen by the pacemaker. Thus, for example only, by making the vent holes 60 about 0.006 inches in diameter and approximately 0.071 inches in length, the impedance requirements of the specification are met while still allowing adequate venting. Other diameter/length parameters can also be selected to yield the desired impedance value.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself

What is claimed is:

1. A header for an implantable medical device, said device comprising an electronic circuit and a power source contained within a hermetically sealed housing and having a feedthrough with a plurality of input and output pins, the header comprising:

(a) a plastic connector module of generally rectangular cross section with a top surface, a bottom surface and first and second side edges, said module having a longitudinal bore adapted to receive a lead connector pin therein, the connector module having a plurality of spaced apart, transversely extending slots formed through one of the first and second side edges of said connector module and intersecting the longitudinal bore and having a corresponding plurality of pin-hole apertures formed in a bottom surface of the connector module and individually intersecting with the plurality of transversely extending slots;

(b) a plurality of electrical contact members each contact member including a metal plate having a central aperture formed therethrough, the aperture containing a toroidal, canted-coil, metal spring, one such electrical contact member being individually inserted through each of said slots such that the central aperture of each of the contact members is coaxial with the longitudinal bore;

(c) a tubular elastomeric seal member disposed in the longitudinal bore between adjacent ones of the contact members with opposed ends of the seal member abutting adjacent ones of the contact members; and (d) each of said metal plates being conductively attached to an individual one of the input and output pins with the input and output pins passing individually through the plurality of pin-hole apertures formed in the bottom surface of the connector module.

2. The header of claim 1 wherein the input and output pins are conductively attached to an individual one of the metal plates by welding.

3. The header of claim 1 wherein the slots are generally D-shaped and the electrical contact members are also generally D-shaped to minimize a width dimension of the connector port.

4. The header of claim 1 wherein the contact members are round and the slots are shaped to receive the round contact members therein.

5. The header of claim 1 wherein the connector module includes a further transversely extending slot intersecting the longitudinal bore at an inner end thereof; and a lead connector pin locking member disposed in the further slot.

6. The header as in claim 5 wherein the locking member comprises an insert having a first bore therein coaxial with the longitudinal bore when the insert is disposed in the further slot and a threaded bore intersecting the first bore; and a set-screw in the threaded bore for engaging a proximal end portion of a lead connector pin inserted through the longitudinal bore of the connector module into the first bore of the insert.

7. The header as in claim 1 and further including a vent hole formed in the plastic connector module in fluid communication with an inner end portion of the longitudinal bore for venting pressurized air as a lead connector pin is being inserted into the longitudinal bore.

8. The header pin as in any one of claims 1–7 wherein the tubular elastomeric seals comprise a generally cylindrical body with integrally formed spaced-apart ribs projecting radially outward and inward from said cylindrical body, the outwardly projecting ribs engaging the longitudinal bore of the connector module and the inwardly projecting ribs engaging a lead connector pin when said lead connector pin is inserted into the longitudinal bore and through the tubular elastomeric seals.

9. A header for an implantable medical device, said device comprising an electronic circuit and a power source contained within a hermetically sealed housing and having a feedthrough plate with a plurality of input and output pins extending through the feedthrough plate, the header comprising:
   (a) a plastic connector module of generally rectangular cross-section with a top surface, a bottom surface and two opposed side surfaces and having a longitudinal bore extending inward from one end thereof adapted to receive a lead connector pin therein, the connector module having a plurality of spaced apart, transversely extending slots formed through one of the opposed side surfaces of said connector module and intersecting the longitudinal bore;
   (b) a plurality of electrical contact members sized to conform to said slots and inserted therein, each contact member including a metal plate having a central aperture formed therethrough; and
   (c) a tubular elastomeric seal member disposed in the longitudinal bore between adjacent ones of the contact members with opposed ends of the seal member abutting adjacent ones of the contact members.

10. The header of claim 9 and further including a toroidal metal spring disposed in the aperture.

11. The header of claim 9 wherein the plastic connector module further includes:
   (a) a plurality of pin-hole apertures formed in the bottom surface of the connector module and individually intersecting one of the plurality of transversely extending slots, said pin-hole apertures adapted to receive input and output pins of the feedthrough plate therethrough.

12. The header of claim 11 wherein the connector module has a generally rectangular recess formed in the bottom surface for receiving the feedthrough plate therein.

13. The header of claim 12 wherein the input and output pins are individually welded to a surface of the electrical contact members that is exposed through the slot in which the contact member is inserted.

14. A method of assembling a header for an implantable medical device comprising the steps of:
   (a) providing a molded plastic connector module of generally rectangular cross-section with a top surface, a bottom surface and two opposed side surfaces and having a longitudinal bore adapted to receive a lead connector pin therein, the connector module having a plurality of spaced-apart, transversely extending slots formed through one side surface of said connector module and intersecting the longitudinal bore;
   (b) providing a plurality of electrical contact members each comprising a metal plate having an aperture extending through a thickness dimension thereof, the apertures containing a contact adapted to mate with the lead connector pin;
   (c) providing a plurality of tubular, generally cylindrical, elastomeric seal members of an outer diameter corresponding to that of said longitudinal bore;
   (d) alternately inserting a seal member down the longitudinal bore and an electrical contact member into a transversely extending slot in that order, proceeding from an inner end of the longitudinal bore to the an outer end thereof until each of the transversely extending slots has received one of the plurality of electrical contact members and such that an inserted one of the plurality of electrical contact members acts as a limit for the depth of insertion of a next inserted seal member.

\* \* \* \* \*